May 7, 1940. C. B. HANSEN Plant Pat. 389
ROSE
Filed May 25, 1939
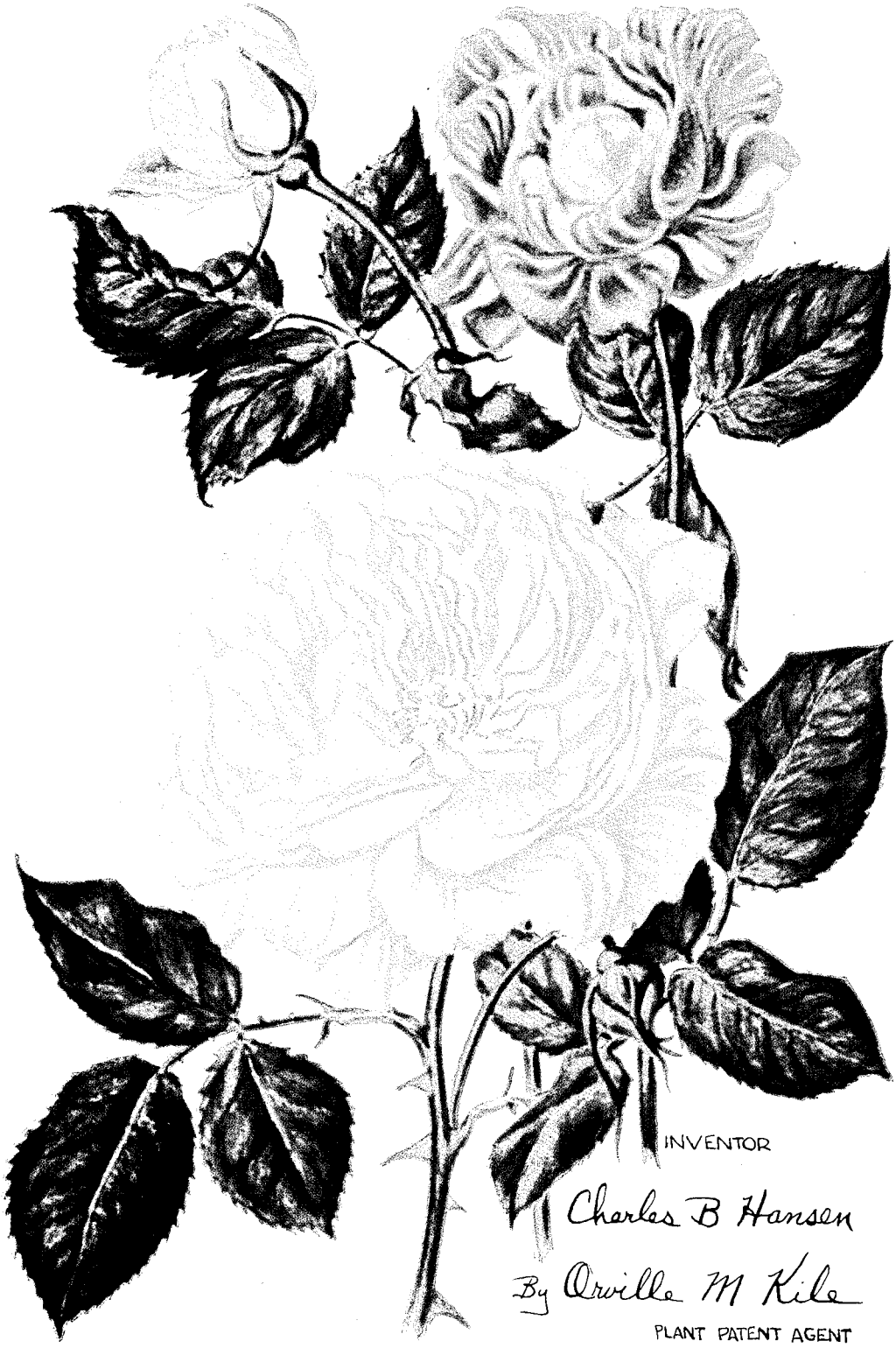

Patented May 7, 1940

Plant Pat. 389

UNITED STATES PATENT OFFICE

389

ROSE

Charles B. Hansen, Ontario, Calif.

Application May 25, 1939, Serial No. 275,750

1 Claim. (Cl. 47—61)

This new variety is of the hybrid tea class and originated as a sport of the rose Queen Alexandra. It was discovered by me on my residence property as a branch of a Queen Alexandra plant which had been budded as a standard rose. It resembles its parent in most respects but differs particularly in the color of its blossoms. The new variety has been reproduced asexually by budding and has retained its characteristics.

The distinctive feature of this new variety is the production of variegated flowers in bright rose and pale yellow shades. It differs from other varieties of variegated roses in that it has a much higher degree of brilliance and contrast in the colors present in the rose and also in the high degree of variegation.

The original illustrations accompanying this application show three specimens of this variety in various stages of opening, together with a portion of the stems and leaves.

These are typical specimens but it must be understood that the amount of variegation varies greatly, although the same basic colors are found.

Following is a detailed description of this new variety of rose. Color plate references indicate Ridgway's Color Standards and Nomenclature. Where plate references are not given the ordinary dictionary term is intended.

*The plant*

Growth: Low and spreading; where well grown, attains a spread of four feet and a height of three feet.

Blooming habit: Very profuse bloomer throughout the growing season.

Disease resistance: Very resistant to mildew and black spot.

Stems: Cedar Green (Plate VI); medium to short; strong and straight at base; have numerous thorns.

*Thorns.*—Tinged reddish when young and greyish-brown when mature. Most of them are large with a broad base but a few are small and slender. Point is usually straight but sometimes slightly hooked. Direction is slightly downward-pointing.

Foliage:

*Leaves.*—Compound, with 3 to 5 leaflets; small; tough; Dark Cress Green (Plate XXXI): glossy. Leaflets—shape—lateral leaflets pointed-elliptical; terminal leaflets almost round but with sharp point at apex. Edge finely serrated. Size—lateral leaflets 1 inch broad by 1½ inches long; terminal leaflets about same length but 1¼ to 1½ inches broad.

*Rachis.*—Slender; upper side grooved; lower side thorny.

*Stipules.*—Extremely narrow, with long narrow points.

*The flower*

Bud:

*Shape.*—Pointed-globular.

*Size.*—Medium to large, averaging 1¼ to 1½ inches in length. Averages approximately 1 inch broad at its base.

*Color.*—Rose Color (Plate XII), with striped variegations of Maize Yellow (Plate IV) and Buff Yellow (Plate IV). Inside of opening bud is velvety Tyrian Rose (Plate XII) with stripings of Maize Yellow to Buff Yellow.

*Peduncle.*—Covered with numerous short spines and occasional small short thorns. Usually slightly curved or nodding but sometimes straight. Strong at base, tapering to slender tips.

Bloom:

*Size.*—Medium to large, averaging 3½ to 4 inches in diameter. Occasionally larger.

*Form.*—Cupped at first, later opening flat. When fully open the petals roll backward slightly but do not quill.

*Color.*—The principal color of the inner surface of the petals of the fully opened flower lies between Rose Color and Tyrian Rose (Plate XII), and is variegated with radial stripes and splashes ranging from Cream Color (Plate XVI) to Maize Yellow (Plate IV). The under surface of the petals is Thulite Pink (Plate XXVI) with variegations of Cream Color (Plate XVI). The base of the petals is between Lemon Yellow and Lemon Chrome (Plate IV).

*Petalage.*—In January the petalage numbers about 32 petals.

*Petals.*—Texture—smooth; medium heavy. Shape—modified truncate or wedge-shaped. Aspect—under surface dull; upper surface velvety in opening flower, becoming more shiny as it opens and finally having a translucent appearance.

*Behavior.*—Opens slowly to cup-shaped blooms; keeps extraordinarily well; petals cling tenaciously. These features are especially good for shipping purposes. A blossom which was shipped from California to Washington, D. C., lasted five or six days after arrival.

*Fragrance.*—Has the same rich spicy fragrance found in the flowers of Queen Alexandra.

*Sepals.*—Usually not foliaceous but occasionally slightly so.

*Reproductive organs*

Stamens: Long; uneven; surround pistils and sometimes intertwine with them.

*Filaments.*—Light Cadmium (Plate IV) uneven lengths.

*Anthers.*—Approximately Primuline Yellow (Plate XVI); medium size.

Pistils: Many; bunched.

*Styles.*—Long; white; hairy.

*Stigmas.*—Light Orange Yellow (Plate III).

*Pollen.*—From Cadmium Yellow (Plate III) to Light Cadmium (Plate IV).

Having thus disclosed my discovery, I claim:

A new and useful variety of hybrid tea rose, substantially as shown and described, characterized particularly by its low, spreading growth; its prolific production of blossoms; its resistance to disease; and its large variegated blossoms of Rose to Tyrian Rose with radial stripings and splashings of Cream to Maize Yellow.

CHARLES B. HANSEN.